US011730696B2

(12) United States Patent
Tuch et al.

(10) Patent No.: US 11,730,696 B2
(45) Date of Patent: Aug. 22, 2023

(54) CELL ASSOCIATED SCAFFOLDS FOR DELIVERY OF AGENTS

(71) Applicant: AUSTRALIAN FOUNDATION FOR DIABETES RESEARCH, Maroubra (AU)

(72) Inventors: Bernard Tuch, Maroubra (AU); Tim Dargaville, The Gap (AU); Auvro Mridha, Glenfield (AU); Paul Dalton, Bavaria (DE); Vijayaganapathy Vaithilingam, Pondicherry (IN)

(73) Assignee: AUSTRALIAN FOUNDATION FOR DIABETES RESEARCH, Maroubra (AU)

( * ) Notice: Subject to any disclaimer, the term of this patent is extended or adjusted under 35 U.S.C. 154(b) by 0 days.

(21) Appl. No.: 16/340,555

(22) PCT Filed: Oct. 18, 2017

(86) PCT No.: PCT/AU2017/051126
§ 371 (c)(1),
(2) Date: Apr. 9, 2019

(87) PCT Pub. No.: WO2018/071967
PCT Pub. Date: Apr. 26, 2018

(65) Prior Publication Data
US 2019/0254959 A1    Aug. 22, 2019

(30) Foreign Application Priority Data
Oct. 20, 2016   (AU) ................ 2016904265

(51) Int. Cl.
| | | |
|---|---|---|
| *A61K 9/00* | (2006.01) | |
| *A61L 27/54* | (2006.01) | |
| *A61L 27/56* | (2006.01) | |
| *A61L 27/20* | (2006.01) | |
| *A61K 35/39* | (2015.01) | |
| *A61L 27/38* | (2006.01) | |
| *A61P 3/10* | (2006.01) | |
| *A61K 47/34* | (2017.01) | |
| *A61F 2/02* | (2006.01) | |
| *B33Y 80/00* | (2015.01) | |
| *B33Y 70/00* | (2020.01) | |
| *A61K 38/28* | (2006.01) | |
| *A61L 27/18* | (2006.01) | |
| *A61P 1/16* | (2006.01) | |
| *A61P 25/16* | (2006.01) | |
| *B33Y 10/00* | (2015.01) | |
| *A61F 2/00* | (2006.01) | |
| *A61K 35/12* | (2015.01) | |

(52) U.S. Cl.
CPC ........... *A61K 9/0024* (2013.01); *A61F 2/022* (2013.01); *A61K 35/39* (2013.01); *A61K 38/28* (2013.01); *A61K 47/34* (2013.01); *A61L 27/18* (2013.01); *A61L 27/20* (2013.01); *A61L 27/3804* (2013.01); *A61L 27/54* (2013.01); *A61L 27/56* (2013.01); *A61P 1/16* (2018.01); *A61P 3/10* (2018.01); *A61P 25/16* (2018.01); *B33Y 80/00* (2014.12); *A61F 2002/0086* (2013.01); *A61K 2035/128* (2013.01); *A61L 2300/252* (2013.01); *A61L 2300/43* (2013.01); *A61L 2300/62* (2013.01); *A61L 2300/64* (2013.01); *B33Y 10/00* (2014.12)

(58) Field of Classification Search
None
See application file for complete search history.

(56) References Cited

U.S. PATENT DOCUMENTS

| | | | | |
|---|---|---|---|---|
| 10,034,963 | B2 * | 7/2018 | Hasilo | ............... A61L 27/58 |
| 2010/0092433 | A1 | 4/2010 | Levenberg et al. | |
| 2010/0215713 | A1 * | 8/2010 | Dolmans-Van Der Vorst | ............ A61P 15/08 514/474 |
| 2010/0292791 | A1 * | 11/2010 | Lu | ............... A61F 2/0811 623/13.12 |
| 2010/0327494 | A1 * | 12/2010 | Jabbari | ............... B29C 48/02 264/466 |
| 2015/0056471 | A1 * | 2/2015 | Joo | ............... C04B 35/6224 428/687 |
| 2021/0022871 | A1 * | 1/2021 | Castro | ............... A61F 2/30942 |

FOREIGN PATENT DOCUMENTS

| | | | |
|---|---|---|---|
| WO | 2005/005609 | | 1/2005 |
| WO | 2011/025977 | | 3/2011 |
| WO | WO 2011088365 | * | 7/2011 |
| WO | 2011/130322 | | 10/2011 |

(Continued)

OTHER PUBLICATIONS

Proulx, Tom "MEMS and Nanotechnology, vol. 2:Proceedings of the 2010 Annual Conference on Experimental and Applied Mechanics" Article: Wanasekara et al. "Ivnestigation of the Youn's Modulus of Fibers in Electrospun PCL Scaffold using AFM and its Correlation to cell Attachment" 2011.*
Bruzauskaite et al. "Scaffolds for tissue regernation: different scaffold pore sizes—different cell effects" 2015.*
Bonvallet, et al., "Microporous Dermal-Mimetic Electrospun scaffolds Pre-Seeded with Fibroblasts Promote Tissue Regeneration in Full-Thickness Skin Wounds," PLOSone, Mar. 20, 2015, 17 pgs., 10(3).
Kasoju, et al., "In Vivo Vascularization of Antisotropic Channeled Porous Polylactide-Based Capsules for Islet Transplantation: The Effects of Scaffold Architecture and Implantation Site," Physiological Research, 2015, pp. S75-S84m vol. 64.
Linn, et al., "Polymers for Induction of Revascularization in the Rat Fascial Flap: Application of Vascular Endothelial Growth Factor and Pancreatic Islet Cells," Cell Transplantation, 2003, pp. 769-778, vol. 12.

(Continued)

Primary Examiner — Danah Al-Awadi
(74) Attorney, Agent, or Firm — Lowenstein Sandler LLP (57) ABSTRACT

The present invention relates to the use of scaffolds to enhance the viability of cells implanted in the integumentary system such that the cell may release an agent. The scaffold is capable of protecting the cell, as well as allowing for adequate nutrient delivery at the implant site through vascularisation in and around the scaffold.

14 Claims, 8 Drawing Sheets

(56) References Cited

FOREIGN PATENT DOCUMENTS

| WO | WO 2011130322 | * 10/2011 |
|---|---|---|
| WO | 2012/048170 | 4/2012 |

OTHER PUBLICATIONS

Mavila, et al., "Functional Human and Murine Tissue-Engineered Liver Is Generated from Adult Stem/Progenitor Cells," Stem Cells Translation Medicine, 2016, pp. 238-248, vol. 6.

Thibaudeau, et al., "A tissue-engineered humanized xenograft model of human breast cancer metastasis to bone," Disease Model & Mechanisms, 2014, pp. 299-309, vol. 7.

Tuch, et al., "Scaffolds for islets and stem cells differentiated into insulin-secreting cells," Frontiers in Bioscience, pp. 126-138, vol. 19.

Mago, et al., "The reversal of hyperglycaemia in diabetic mice using PLGA scaffolds seeded with islet-like cells derived from human embryonic stem cells," Biomaterials, 2009, pp. 1706-1714, vol. 30, No. 9.

Fabryova, et al., "The optimal timing can improve engraftment of pancreatic islets transplanted into the subcutaneous cavity," Xenotransplantation, 2015, p. S103, Abstract No. 610, Supplement 1, vol. 22.

Muerza-Cascante, et al., "Melt Electrospinning and Its Technologization in Tissue Engineering," Tissue Engineering: Part B, 2015, pp. 187-202, vol. 21, No. 2.

Supplementary European Search Report for EP17862669 dated Apr. 17, 2020, 8 pages.

* cited by examiner

CELL ASSOCIATED SCAFFOLDS FOR DELIVERY OF AGENTS

CROSS-REFERENCE TO RELATED APPLICATION(S)

This application is a national phase entry under 35 U.S.C. § 371 of International Application No. PCT/AU2017/051126, filed on Oct. 18, 2017, which claims the benefit of priority of Australian Patent Application No. 2016904265, filed on Oct. 20, 2016. The contents of these applications are hereby incorporated by reference herein in their entirety.

FIELD OF THE INVENTION

The present invention relates to methods of delivering an agent to a subject using scaffolds. In particular, the invention relates to the use of scaffolds to implant cells that release therapeutically beneficial agents into the integumentary system.

BACKGROUND

Cell therapies requiring implantation are currently being developed to treat a variety of medical conditions. For example, insulin-dependent diabetes, liver failure and Parkinson's disease can be treated or alleviated by the delivery of agents released by particular cells implanted into the patient.

Effective cell therapy is challenging, as the viability of the implanted cells may be compromised due to lack of physical protection and/or insufficient amounts of growth factors and nutrients after implantation. Cell viability can also be hindered by a lack of adequate vascularisation required to deliver oxygen and nutrients to the cells at the site. Implanted cells are also susceptible to immune responses from the host, wherein the host essentially rejects the implanted cells, commonly referred to as the host cell response.

Accordingly, implantation of cells generally needs to be accompanied by some means of immunosuppression, and this is often provided in the form of anti-rejection drugs or immunosuppressive drugs. These drugs must be taken prior to or at the time of implantation (often at high doses), and then must be maintained at lower doses after implantation, and include a range of agents such as immunophillin-binding agents, anti-proliferative agents, antibodies and steroids. It would be understood that there are inherent risks associated with any drug that is administered to deliberately compromise the immune system of a subject, and that many of the immunosuppressive drugs used also have toxic side-effects. These toxic side-effects can include an increased risk of infection and development of cancer. Accordingly, there is a need for means to minimise the host cell response to implanted cells and reduce the need for immunosuppressive drugs before and after implantation.

To protect the cells from the immune system of the host, cells are also sometimes placed in bioengineered immuno-isolation devices, such as alginate microcapsules, prior to implantation. This method has been shown to reduce the need for immunosuppressive drugs ordinarily required to suppress the immune system and hence allow the implanted cells to survive and function.

However, the host still reacts to the microcapsules, often forming fibrotic reactions around them, as the immune system of the host recognizes them as foreign bodies. The fibrotic tissue reduces the porosity of the microcapsules, and this can cause death of the encapsulated cells.

Implantation of cells in the subcutaneous layer of the skin may alleviate many of these problems, as the cells may be less susceptible to the host fibrotic reaction due to there being fewer host macrophages, as compared to, for example, the peritoneal cavity where the reaction is greater. A disadvantage of subcutaneous implantation, however, is the much lower blood supply available in this region. Without access to a fully developed vasculature, the supply of oxygen and other nutrients to the implanted cells is reduced. In the absence of sufficient blood flow to the cells and the cell's microenvironment, it is difficult to maintain the viability of the cells for extended periods of time. Moreover, the means of implantation needs to provide adequate mechanical protection and spatial distribution of the implanted cells in a region that may experience more external pressures than the peritoneal cavity.

Accordingly, the subcutaneous space could serve as an ideal implantation site, if challenges of low oxygen tension and poor vascularity could be overcome and mechanical protection to implanted cells provided.

The ability to maintain the viability of implanted cells in a host is of particular interest to the field of diabetes research. Type 1 diabetes is an auto-immune condition in which the host's immune system destroys the beta-cells in the pancreas, the islets, which produce insulin. There is no known cure for the disease. Implantation of islets to a diabetic subject has shown potential as a long term-treatment to normalise blood glucose levels in subjects and reduce insulin dependency.

As is the case with many cell therapies, implantation of insulin-producing cells has been hindered by the inability to maintain the viability of the cells for durations that would have clinical relevance because of a combination of host-immune response and/or insufficient blood flow to the implanted cells. In general, research has focused on intra-hepatic and/or intraperitoneal implants. However, these therapies result in undesirable host cell responses and necessary exposure to anti-rejection drugs, which can lead to toxic side effects, infections and cancer.

Strategies to overcome these difficulties have been labour-intensive or unsuccessful in the long term. They have relied on methods such as prevascularisation of an implantation site, or use of rigid devices and/or capsules that have elicited inflammatory responses that cause fibrosis, which ultimately blocks the blood supply to the implanted cells.

As such, there is a need for methods and scaffolds for the implantation of cells that can both (a) reduce the host cell response to the cells without the need for immunosuppressive drugs, and (b) enhance the viability of the implanted cells though adequate vascularisation providing sufficient access to nutrients and oxygen.

The present inventors have found that the suitability of the integumentary system as an implantation site may be increased by placing cells in porous three-dimensional scaffolds along the strands of which host blood vessels can grow. This delivers nutrients to the cells thereby allowing the cells to survive and function, even in the event there is a foreign body reaction/host cell response to the implanted device. The likelihood of a significant host cell response is reduced as the scaffold is implanted in a region with fewer macrophages.

The present inventors have also found that, by utilising such scaffolds that promote vascularisation at the site of implantation, implantation of insulin-producing cells in the integumentary system can be used for the long-term treatment and/or prevention of diabetes. Advantageously, the scaffolds may also be used in conjunction with encapsulated cells to further minimise the host immune response against the cells.

SUMMARY OF THE INVENTION

The present invention relates to the use of scaffolds to enhance the viability of cells implanted in the integumentary system such that the cell may release an agent. The scaffold is capable of protecting the cell from mechanical stresses, as well as allowing for adequate nutrient delivery at the implant site through vascularisation in and around the scaffold.

According to a first aspect of the present invention, there is provided a method for delivering an agent to a subject, comprising associating a cell that produces said agent with a scaffold, and implanting said scaffold-associated cell subcutaneously.

According to a second aspect of the present invention, there is provided a scaffold for subcutaneous implantation of a scaffold-associated cell, wherein said scaffold enhances the viability of the scaffold-associated cell after implantation by promoting vascularisation at the site of implantation.

The integumentary system is the organ system that protects the body from external elements, and comprises the skin. The skilled addressee would appreciate that the skin is made up of layers, including the epidermis, dermis and hypodermis (subcutaneous layer), as well as other components such as adipose tissue, hair follicles, veins, arteries, sweat glands and nerve fibres. The scaffold may be implanted in the epidermis, dermis or subcutaneous layer, or in a region that traverses more than one layer. The scaffold may be implanted in skin on any part of the subject's body. A subject may be implanted with more than one scaffold. A scaffold may comprise more than one type of scaffold-associated cell. When more than one scaffold is implanted, the scaffolds may have the same scaffold-associated cells (or mix of cells) or they may have different scaffold-associated cells (or mixes of cells).

In preferred embodiments of the invention, the scaffold is implanted in the subcutaneous layer of the skin of a subject. It would be understood that by this is meant that, immediately after implantation, at least a portion of the scaffold and some scaffold-associated cells are positioned in the subcutaneous layer of the skin.

The scaffold enhances the viability of the cell such that the cell can produce said agent for a duration that is greater than that expected to be achieved if the cell were to be implanted at the same site without said scaffold. For example, in the absence of the scaffold, a cell implanted in the subcutaneous layer of the skin may be capable of producing said agent, at least temporarily, until such time as the host recognises the cell as a foreign body, which would result in the cell being destroyed by the host immune response. By implanting the same cell after being associated with the scaffold, the host cell response may be reduced or delayed, thereby allowing the cell to produce the agent for a longer period of time.

Accordingly, in an embodiment of the invention, the scaffold reduces or delays the host cell response of the subject to the scaffold-associated cell when compared to the host cell response of the subject if the same cell type were to be implanted subcutaneously without said scaffold.

By reducing or delaying the host cell response that would ordinarily be triggered if the cell were to be subcutaneously implanted without being associated with a scaffold, the use of the scaffold may result in the subject requiring less immunosuppressive drugs either before during or after implantation, and/or requiring immunosuppressive drugs for a shorter duration. For example, a subject implanted with a scaffold-associated cell may require a lower dose of immunosuppressive drugs prior to implantation than a subject implanted with the cell alone. In another example, a subject implanted with a scaffold-associated cell may require a lower dose of immunosuppressive drugs for a shorter period of time after the implantation than a subject implanted with the cell alone.

In another example, in the absence of the scaffold, a cell implanted in the subcutaneous layer of the skin may be capable of producing and releasing an agent, at least temporarily, until such time as the insufficient access to nutrients and oxygen due to poor vascularisation of the implantation site causes the cell to die or become quiescent. By implanting the same cell after being associated with the scaffold, vascularisation is promoted at the site of implantation, thereby allowing for adequate nutrient delivery to the cell and delaying or preventing cell death or quiescence. This would allow the cell to produce and release the agent for a longer period of time.

The scaffold also allows for spacial distribution of the cells at the implant site and/or reduces the aggregation and/or destruction of cells by providing structural support.

In certain embodiments, the scaffold allows and promotes vasculogenesis and angiogenesis in and around the scaffold, thereby enhancing the delivery of nutrients and growth factors necessary for the viability of cells at the implant site. It would be understood that vasculogenesis and angiogenesis are complementary processes that ultimately lead to vascularisation of and around the site of implantation. The vascularisation also enhances the circulation and distribution of the agent produce and released by the scaffold-associated cell. Vascularisation of the site of implantation may be determined qualitatively and/or quantitatively by, for example, microscopic methods and histological methods utilising endothelial cell markers.

In embodiments of the invention, the scaffold increases vascularisation at the site of subcutaneous implantation when compared to subcutaneous implantation of the same cell type without said scaffold.

In some embodiments, the scaffold allows for the implanted cells to be removed if required.

By "associating a cell" or "scaffold associated cell" is meant that the cell is partially or fully encased within the scaffold and/or is touching the scaffold and/or is adhered to the scaffold.

The agent may be any agent that is therapeutically beneficial to the subject. In preferred embodiments, a deficiency of said agent is a causative factor of a disease or disorder and in such embodiments, it would be understood that said agent may, reduce or redress, at least temporarily, the deficiency of the agent in the subject, thereby treating or preventing the disease or disorder.

The disease or disorder being treated or prevented may be any disease or disorder that may be treated or prevented by an agent that is capable of being released by a cell. The disease or disorder being treated or prevented may, for example, be diabetes, Parkinson's disease or another chronic neurodegenerative disease, haemophilia, liver failure, anaemia or a psychiatric disorder that results from low levels of appropriate neurotransmitters. The agent may be insulin, C-peptide, glucagon, erythropoietin, Factor VIII, Factor IX, haemoglobin, albumin, dopamine, serotonin, norepinephrine, epinephrine, parathormone, thyroxine, or tri-iodothyronine.

The agent may be any agent that can be produced by a cell. The agent may be produced by the cell at any time while the cell is associated with said scaffold. For example, the cell may produce the agent continuously once the cell is associated with the scaffold. In another example, the cell may only produce the agent after subcutaneous implantation. In other example, the cell may only produce the agent after the implantation site is sufficiently vascularised. In further examples, the cell may only produce the agent intermittently or in response to external stimuli after implantation. Preferably, the agent is released by the cell. More preferably, the agent is released proportionally to the manner in which it is produced by the cell.

The scaffold-associated cell may be any cell that is capable of producing and releasing an agent. For example, the cell may be capable of regulating blood glucose levels and may be useful for the treatment or prevention of diabetes because it produces and releases an agent, such as, for example, insulin or glucagon.

In preferred embodiments, the agent is insulin, an insulin analog, or a precursor of insulin, such as preproinsulin or proinsulin.

The scaffold-associated cell may be derived from any tissue and may be of non-human or human origin. The scaffold-associated cell may be derived from the host or from another source. The cell may be a recombinant cell. It may be from an immortalised cell line or a primary differentiated cell line. For example, the scaffold-associated cell may be an immortalised cell line derived from a mouse, human, rat or pig. The scaffold-associated cell may be a mature cell, or an immature cell that is capable of maturing to produce an agent after implantation.

In preferred embodiments, the scaffold-associated cell is a cell derived from a mammalian pancreas. In further preferred embodiments, the scaffold-associated cell is an immortalised pancreatic beta cell. In other embodiments, the scaffold-associated cell is derived from a stem cell.

The agent may be endogenous to the cell, and may be produced and released constitutively or in response to a stimulus. Alternatively, the agent may be a recombinant product produced and released by a scaffold-associated cell that has been genetically modified, and may do so constitutively or in response to a stimulus.

For example, the scaffold-associated cell may produce and release an agent capable of regulating blood glucose levels in response to an increase in a subject's blood glucose level. In another example, the scaffold-associated cell may release an agent capable of regulating blood glucose levels constitutively, but may cease releasing said agent in response to a decrease in a subject's blood glucose level. In other examples, the scaffold-associated cell may be any insulin-producing cell that releases insulin in response to increased blood glucose levels.

In another example, the scaffold-associated cell may be genetically modified and release a recombinant agent after expression of said agent from an expression system with a glucose- or glycogen-sensitive promoter. The scaffold-associated cell may be a genetically modified cell that expresses and releases insulin, an insulin analog, or a precursor of insulin, such as preproinsulin or proinsulin in response to a stimulus related to blood glucose levels.

The scaffold-associated cell may release more than one therapeutically beneficial agent. The scaffold may be associated with more than one type of cell, wherein each type of cell releases a therapeutically beneficial agent. In this instance, each type of cell associated with the scaffold may release a different therapeutically beneficial agent, or the same therapeutically beneficial agent. The cells associated with the scaffold may release different agents in response to different stimuli, they may release the same agents in response to different stimuli, or they may release the same agent in response to the same stimuli.

The scaffold may be associated with an additional cell that enhances the viability of the scaffold-associated cell releasing the agent. For example, the scaffold may be associated with one or more additional cells selected from the group consisting of a mesenchymal and/or bone marrow derived cell, an endothelial progenitor cell or a stem cell. These additional cells may be chosen such that they enhance the delivery of nutrients and growth factors to the implant site by, for example, accelerating vasculogenesis and angiogenesis in and around the scaffold. The improved blood flow to the scaffold-associated cell achieved in a shorter amount of time due to the presence of the additional cell may further enhance the viability of the cell releasing the agent.

In one or more embodiments of the invention, the disease or disorder is diabetes and the agent is insulin. Preferably, the scaffold-associated cell is an insulin producing cell or a pancreatic islet cell that is capable of producing and releasing insulin.

It would be understood that implanting, in a subject with diabetes, a scaffold-associated cell that produces and releases insulin in response to an increase in said subject's blood glucose level, such as, for example, a pancreatic islet cell or pseudoislet cell, could assist in the regulation of blood glucose levels, thereby treating or preventing diabetes and rendering the subject less dependent on administered insulin.

In preferred embodiments of the present invention, the cell is encapsulated prior to being associated with the scaffold. In the context of the present invention, the process of encapsulation is the trapping of a cell or cells in a porous material. The porosity of the material allows for effective release of the agent. In certain embodiments, the porous material protects the cell from the immune system (i.e., a host cell reaction). In some embodiments, the porous material allows the transfer of oxygen and/or nutrients to the cell.

The encapsulation may enhance the viability of the scaffold-associated cell such that the cell can produced and release the agent for a duration that is greater than that expected to be achieved if the scaffold-associated cell were not encapsulated. The encapsulation may also reduce or delay the host cell response to the encapsulated scaffold-associated cell when compared to the host cell response if the subject was implanted with a scaffold associated cell that was not encapsulated. For example, an unencapsulated scaffold-associated cell implanted in the subcutaneous layer of the skin may potentially still be recognised as a foreign body by the host, which may result in the cell being destroyed by the host cell response. By encapsulating the same cell prior to being associated with the scaffold and implanted, the host cell response may be delayed or minimised and/or the need for immunosuppressive drugs may be reduced or the duration shortened, thereby allowing the cell to release the agent for a longer period of time.

The encapsulation material may be any material that undergoes gelation. The encapsulation material may be biodegradable and/or biocompatible. In certain embodiments of the invention, the cell is encapsulated in a hydrogel. It would be understood that hydrogels are generally water swellable, water insoluble, cross-linked, porous networks with elastic properties.

The cell may be individually encapsulated or a number of cells may be enclosed in one capsule. In embodiments, the cell is individually encapsulated. In other embodiments, cell clusters are encapsulated.

The cell may be encapsulated in any suitable biocompatible material, including, but not limited to, alginate, poly(ethylene glycol) (PEG), collagen, fibrin, cellulose, gelatine, agarose, and/or combinations thereof. The material may be derived from nature, produced recombinantly or synthetically, or a combination of natural, synthetic or recombinantly produced material. In preferred embodiments of the invention, the cell is encapsulated in alginate prior to being associated with the scaffold.

The scaffold may be any rigid or semi-rigid scaffold that can provide the structural support required for the implantation of a scaffold-associated cell into the integumentary system of a subject. The scaffold may be any shape or size that is suitable for subcutaneous implantation in a subject. Generally, the scaffold will comprise fibres that are arranged in such a way as to surround, or partially surround void spaces, referred to as pores. Pores may be in communication with adjacent pores, and this may be achieved by, for example, the fibres being arranged in a manner that does not form solid walls between the pores, in that the walls have gaps. Advantageously, this enhances the flow of nutrients and growth factors throughout the scaffold by encouraging vasculogenesis and angiogenesis in and around the scaffold, thereby enhancing the viability of the scaffold-associated cells. In preferred embodiments, the scaffold-associated cells cannot migrate between the pores.

In preferred embodiments of the invention, the scaffold comprises biocompatible and/or biodegradable fibres. The fibres may be any thickness required to achieve the desired scaffold structure and pore size. The thickness of the fibre may also be determined by the type of biocompatible material or fabrication method used. The scaffold may be comprised of fibres with varying thickness along the length of the fibre. The scaffold may be comprised of fibres with uniform, but different thicknesses. By "thickness" is meant the measurement of a cross-section of the fibre perpendicular to the length of the fibre.

In preferred embodiments, the fibres are 1-200 µm thick. For example, the fibres may be 100-20 µm, 10-100 µm, 1-100 µm, 10-20 µm, 50-100 µm, 1-50 µm or 20-50 µm thick. Preferably, the fibres are 1-100 µm thick. More preferably, the fibres are 1-50 µm thick. For example, the fibres may be about 10 µm thick, or about 20 µm thick, or about 30 µthick, or about 40 µm thick, or about 50 µm thick.

The scaffolds may comprise fibres made from any suitable biocompatible material, and the scaffolds may be fabricated using any suitable fabrication technique that produces the desired pore size, shape and level of rigidity.

For example, the fibres may comprise a polymer selected from the group consisting of polylactide-co-glycolide, poly-L-lactide (PLLA), polycaprolactone (PCL), polytetrafluoroethylene, polyethylene, polymethyl macralate (PMMA), polylactic acid (PLA), and/or polypropylene (PP) and polyoxaline, and combinations thereof. The scaffold may comprise fibres made from more than one polymer.

Preferably, the fibres comprise polycaprolactone (PCL) and/or polytetrafluoroethylene.

In certain embodiments of the invention, the scaffold is made from fibres comprising non-biodegradable material, such as polyethylene and/or polypropylene. Without wishing to be bound by theory, certain non-biodegradable materials such as polyethylene and/or polypropylene may be preferable over some biodegradable materials, because the biodegradation products of some biodegradable materials may stimulate the host defence system. This host response may lead to clogging of the pores of the scaffold, thereby reducing the effectiveness of the scaffold for enhancing the viability of any associated cells.

The scaffolds may be fabricated using 3D-printing techniques, including but not limited to, stereolithography techniques, fused deposition modelling (FDM), fibre weaving techniques and melt electrospin writing (MEW).

In preferred embodiments of the invention, the scaffolds are fabricated by melt electrospin writing (MEW). Fabricating the scaffolds by MEW allows for tight control over the pore size and shape, and fibre thickness in a reproducible manner. Advantageously, MEW is a solvent-less process that enables the design and fabrication of micrometer-thin fibres with highly controllable architectures and patterns. MEW involves the computer driven high precision fabrication of 3D objects by layer-by-layer deposition of materials onto a movable stage. By altering the digital design file, the shape and pore structure of the scaffold can readily be optimized.

In an embodiment of the invention, the scaffold comprises fibres that are 1-50 µm thick, and fabricated by MEW using a biocompatible polymer. More preferably, the scaffold comprises fibres that are about 15-30 µm thick, and fabricated by MEW using polycaprolactone.

The pores of the scaffold may be any suitable shape or size. The pores may be irregular in shape or may be generally spherical or cubic. A particular scaffold may comprise pores of different shapes and sizes, or may generally comprise pores of the same shape, but different sizes. A particular scaffold may comprise pores of different shapes, but similar sizes.

The size of the pores may be defined in terms of a maximum and minimum dimension, wherein the dimension is any measurement that traverses a pore by passing through the centroid of the pore. The maximum and minimum dimensions may be essentially the same for any given pore, or may be different for any given pore. For example, for a pore that is essentially spherical, both the maximum and minimum dimensions will correspond to the diameter of the spheres in the scaffold. However, for a pore that is an ellipsoid, the maximum dimension is the longest diameter at the major axis, while the minimum dimension is the smallest diameter at the minor axis. A cubic pore will have three dimensions, namely a length, width and height, that will all essentially be the same such that the maximum and minimum dimensions are the same. A rectangular pore will have three dimensions, namely a length, width and height, which will be different such that the maximum and minimum dimensions are different.

In embodiments of the present invention, the scaffold comprises pores that are substantially cubic.

In preferred embodiments of the present invention, the scaffold comprises pores with maximum and minimum dimensions that are conducive to vasculogenesis and angiogenesis in and around the scaffold to enhance the flow of blood to the scaffold-associated cells, and to enhance circulation and distribution of an agent produced and released by the scaffold-associated cell Vasculogenesis is the process of new blood vessel formation, while angiogenesis is the process by which new blood vessels take shape from existing blood vessels and expand the vascular tree. The processes require the migration, differentiation and proliferation of endothelial precursor cells, known as angioblasts, followed by endothelial cell migration, as well as the exchange of metabolic components. These processes result in vascularisation. Accordingly, in preferred embodiments, the scaffold comprises pores with minimum and maximum dimensions to house cells and/or encapsulate cells, whilst also facilitating this migration and exchange around the scaffold-associated cells and through pores that do not house cells.

For example, the scaffold may comprise pores with minimum dimensions of at least 5-250 µM to allow for angiogenesis using existing blood vessels to be effective in and around the scaffold. Preferably, the scaffold comprises pores with minimum dimensions of at least 25-350 µM to allow for effective vasculogenesis in and around the scaffold.

Blood vessels may grow along the fibres of the scaffold, traverse the pores and/or pass between the pores via the gaps in the walls that separate the pores of the scaffolds of the present invention. That the pores of the scaffold have become traversed by blood vessels would be demonstrated by the presence of at least one fully formed blood vessel entering the scaffold at one site and exiting the scaffold at another site. The fully formed blood vessel would be one that is capable of transporting blood. For example, a blood vessel originating outside of the scaffold may continue to grow and enter the scaffold through one pore, pass though at least one more pore in the scaffold and then continue along a fibre that extends to the outer surface of the scaffold. In another example, a blood vessel that has originated from within the scaffold through a process of vasculogenesis may extend outward such that blood vessel passes through the scaffold. In embodiments of the invention, the pores of the scaffold become traversed by blood vessels within 10 weeks of implantation of the scaffold into the subject. In preferred embodiments, the pores become traversed by blood vessels within 5 weeks of implantation of the scaffold into the subject.

In embodiments of the present invention, the scaffold comprises pores with maximum and minimum dimensions that are conducive to housing at least one cell. Preferably, the pore size allows for only one cell to be housed in a particular pore.

In other embodiments, the scaffold comprises pores with maximum and minimum dimensions that are conducive to housing at least one encapsulated cell. Preferably, the pore size allows for only one encapsulated cell to be housed in a particular pore.

The scaffolds of the present invention may comprise pores with maximum and minimum dimensions that are too small to house a single cell. The scaffolds may comprise pores with maximum and minimum dimensions that are too small to house a single encapsulated cell.

In certain embodiments, the scaffold comprises pores with a minimum dimension of at least 100 µm, which is conducive to housing, for example, a pancreatic islet.

In other embodiments, the scaffold comprises pores with a minimum dimension of at least 500 µm, which is conducive to housing, for example, an encapsulated pancreatic islet.

In certain embodiments, the scaffold comprises pores with a maximum dimension of no more than 500 µm, which is conducive to housing, for example, a single pancreatic islet.

In other embodiments, the scaffold comprises pores with a maximum dimension of no more than 2000 µm, which is conducive to housing, for example, a single encapsulated pancreatic islet.

In embodiments of the present invention, the scaffold comprises cubic pores wherein the maximum/minimum dimensions range from 500-1500 µm. In certain embodiments, the scaffold comprises cubic pores wherein the maximum/minimum dimensions range from 500-1000 µm. For example, the scaffold may comprise cubic pores wherein the maximum/minimum dimensions are about 400-600 µm, or about 500-700 µm, or about 600-900 µm, or about 800-1000 µm.

The scaffolds of the invention may also be fabricated to comprise pores with a mixture of pore sizes. In certain embodiments, the scaffold comprises pores with a maximum dimension ranging from 1-2000 µm. The scaffold may comprise pores of different sizes that are randomly distributed, or form localised regions of pores with similar sizes. For example, the scaffold may be fabricated with regions comprising larger pores adjacent to regions that comprise smaller pores. The larger pores may, for example, be conducive to housing cells or encapsulated cells, while the smaller pores may not.

In preferred embodiments, the scaffolds are fabricated with a region comprising smaller pores (a base), a region comprising larger pores (a centre) and (optionally) another region comprising smaller pores (a lid). In this instance, the pores of the lid and/or base would be of a size that did not allow for a cell or an encapsulated cell to be housed, while the pores in the centre would be a size conducive to housing at least one cell or encapsulated cell.

It would be understood that in a scaffold prepared with cells or encapsulated cells housed in pores in a centre region further comprising a lid or base region with pores of a size that did not allow for a cell or an encapsulated cell to be housed, the scaffold-associated cells would be less likely to migrate out of the scaffold.

The scaffold may be fabricated as a single unit with localised regions of different sized pores, such as a scaffold comprising a base region and a centre region, or a scaffold comprising a centre region and a lid region. Alternatively, the scaffold may be fabricated in parts and assembled prior to implantation. For example, a centre region of a scaffold may be fabricated separately from a lid or base region, and the complete scaffold only assembled after cell-association and prior to implantation.

In embodiments of the present invention, the scaffold comprises a lid region and/or a base region comprising pores with a maximum dimension ranging from 1-100 µm. For example, the scaffold may comprise a lid region and/or a base region comprising pores with a maximum dimension ranging from about 1-50 µm, or about 5-25 µm, or about 20-40 µm, or about 30-50 µm. Preferably, the lid region and/or base region comprise cubic pores.

In embodiments of the present invention, the scaffold may comprise a centre region comprising pores with a maximum dimension ranging from 500-1500 µm.

In preferred embodiments of the invention, the scaffold comprises cubic pores, with a lid region and/or base region comprising pores with maximum dimensions ranging from 5-25 µm, and a centre region comprising pores with maximum dimensions ranging from 500-1500 µm. In this particular embodiment, the pores of the lid region and/or base region are large enough to allow host blood vessels to enter and bring nutrients and oxygen to scaffold-associated cells, but are too small to house a cell or encapsulated cell. The pores of the centre region are large enough to allow a single cell or encapsulated cell to be housed, as well as allowing for effective vasculogenesis in and around the scaffold.

In further embodiments, the scaffolds are fabricated with a base, a centre and optionally a lid, and include one or more barrier regions comprising pores that are smaller than the pores of the base and/or the lid. In embodiments, the scaffold comprises one or more barrier regions that are placed between the centre region and the lid and/or the base. In preferred embodiments, the one or more barrier regions comprise pores with maximum dimensions ranging from 0.5-20 µm. The one or more barrier regions may completely or partially separate the centre region from the lid and/or base.

In preferred embodiments of the invention, the scaffold comprises a lid region and a base region comprising pores with maximum dimensions ranging from 5-25 µm, and a centre region comprising pores with maximum dimensions ranging from 500-1500 µm, and the lid region and base region are at least partially separated from the centre region by barrier regions comprising pores with maximum dimensions ranging from 0.5-20 µm.

In other embodiments, the scaffolds are fabricated with a centre and a barrier region comprising pores with maximum dimensions ranging from 0.5-20 µm.

In particular embodiments, the pores of the lid region, the base region and the barrier region are large enough to allow host blood vessels to enter and bring nutrients and oxygen to scaffold-associated cells, but are too small to house a cell or encapsulated cell.

The scaffolds of the present invention may be of any desired shape or size. The shape and size of the scaffolds may be determined by the type or types of scaffold-associated cells to be implanted, the agent to be released, the disease or disorder being treated and/or the location of the implant.

The scaffolds of the present invention may also be associated with one or more molecules that may enhance implantation, the association of the cell with the scaffold and/or the viability of the cell. For example, the fibres or the pores of the scaffold may further comprise adhesion molecules such as extracellular matrix (ECM) proteins including, but not limited to, collagen, fibronectin, laminin, hyaluronic acid, elastin, albumin, fibrin, or RGD peptides. The ECM material may be derived from cells or tissue, it may be synthetic or it may be made recombinantly. The fibres and pores of the scaffold may further comprise polymers that enhance the association of the cell with the scaffold such as, for example, poly-lysine, PEG, agarose or albumin.

The fibres and pores of the scaffold may further comprise molecules such as growth factors, anti-inflammatory factors, immunosuppressive compounds and/or agents that promote vasculogenesis and/or angiogenesis.

Definitions

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

It would be understood that by "biocompatible" is meant that the material is suitable for the implantation in a host. The biocompatible material may be non-toxic and not harmful to humans.

The term "treatment", and the like, in the context of the present specification includes the alleviation of the symptoms related to a disease or disorder or reduction/elimination of the cause of the disease or disorder. In certain embodiments, treatment will reduce the severity of the disease or disorder. In other embodiments, treatment will delay or halt the onset of the disease or disorder. In still other embodiments, treatment will reduce or prevent the spread of the disease or disorder to other parts of the body, at least temporarily. Treatment may cure the disease or disorder characterised by the deficiency of the agent. Hence, in the context of this invention the word "treatment" or derivations thereof when used in relation to a therapeutic application includes all aspects of a therapy, such as the alleviation of pain associated with the disease or disorder, alleviation of the severity of the disease or disorder being treated, improvement in one or more symptoms of the disease or disorder being treated, or improvement in the overall well-being of the subject being treated. Use of the word "treatment" or derivatives thereof will be understood to mean that the subject being "treated" may experience any one or more of the aforementioned benefits.

The term "prevention", and the like, in the context of the present specification refers to the prevention of the recurrence of all or some of the symptoms associated with a disease or disorder characterised by a deficiency of the agent, as well as the prevention of the spread of the disease or disorder.

In the context of this specification the term "about" will be understood as indicating the usual tolerances that a skilled addressee would associate with the given value.

In the context of this specification, where a range is stated for a parameter it will be understood that the parameter includes all values within the stated range, inclusive of the stated endpoints of the range.

In the context of the present invention, the term "subject" refers to an animal, preferably a mammal, most preferably a human, who has experienced and/or exhibited at least one symptom associated with a disease or disorder characterised by a deficiency in an agent. A non-human may be an individual of any species and may be, for example, of social, economic or research importance. In particular, a non-human includes, but is not limited to, members of the classifications of ovine, bovine, equine, porcine, feline, canine, primates, rodents, especially domesticated members of those classifications, such as sheep, cattle, horses and dogs. Further, as used herein, a "subject in need thereof" may additionally be a subject who has not exhibited any symptoms of a disease or disorder characterised by deficiency of an agent, but who has been deemed by, for example, a physician, clinician or other medical professional, a naturopath or other practitioner to be at risk of developing the disease or disorder. For example, the subject may be deemed to be at risk of developing a disease or disorder characterised by a deficiency of an agent (and therefore in need of prevention or preventive treatment) as a consequence of the subject's medical history, including, but not limited to, family history, pre-disposition, co-existing/contributory injuries or disorders and genetic testing.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The present invention is not to be limited in scope by the specific embodiments described herein, which are intended for the purpose of exemplification only. Functionally-equivalent products, compositions and methods are clearly within the scope of the invention, as described herein.

BRIEF DESCRIPTION OF THE DRAWINGS

Embodiments of the invention will now be described, by way of example only, with reference to the accompanying drawings as follows.

FIG. 11: Host cell response to implantation of scaffold-associated cells in immune-competent mice (A) H&E stain shows infiltration of cells in the scaffolds and foci of inflammatory recruitment (arrows) on predominantly on scaffold, but not around microcapsule (*). (B) H&E stain on device under higher magnification showing no foci of inflammatory cells around microcapsule. (C) NF-κB p65+ pro-inflammatory cells localised on scaffolds and not around microcapsule. Similarly (D) MPO+ neutrophils, (E) CD68+ monocyte/macrophages and (F) very few CD19+ B-lymphocytes were all localised to scaffold and not around microcapsules. CD4+ T-lymphocytes were not detectable. Sirius red stain on implant shows ECM deposition of collagen (pink) (G) interconnecting the strands of the scaffold, and (H) around microcapsules. (I) α-SMA+ myofibroblasts showing area of active fibrogenesis around microcapsules and in the scaffold.

DETAILED DESCRIPTION OF PREFERRED EMBODIMENTS

Preferred embodiments of the invention will now be described, by way of example only, with reference to the accompanying drawings.

EXAMPLE 1

Methods
Cell culture:

Monolayers of MIN6 cells (immortalised mouse pancreatic β cell line) were cultured to 50-70% confluency at 37° C. with 5% $CO_2$ in Dulbecco's modified Eagle's medium (DMEM) containing 25 mM glucose supplemented with 10% (v/v) heat-inactivated fetal bovine serum (FBS), 2 mM L-glutamine, 1 mM sodium pyruvate, 100 µM non-essential amino acids, 100 units/mL penicillin and 100 µg/mL streptomycin. Pseudoislets were formed by seeding 1×10$^6$ MIN6 cells in ultra-low attachment 10 cm dishes (Corning Incorp., NY, USA) and culturing for 5 days at 37° C. in 5% CO2. During this time, the cells came together to self-form pseudoislets.

Alginate Encapsulation:

Pseudoislets were pelleted by low speed centrifugation (10×g, 2 min), the culture media was discarded and the loosely pelleted pseudoislets suspended in a highly purified 2.2% alginate solution (60:40 guluronic acid: mannuronic acid, UP MVG PRONOVA, FMC Biopolymer). The pseudoislet/alginate suspension (1:6 packed cell volume: alginate) was transferred to a syringe and inserted into the encapsulation device which consisted of an air-driven droplet generator with a tubing connected to a cylinder of medical grade air. The suspension was infused through the encapsulation device at a rate of 0.67 mL/min with airflow rate of 7 L/min. The flowthrough of droplets was collected in a 20 mM $BaCl_2$ bath for 2 minutes to allow gelling of the capsules. The capsules (~700 µm) containing 1-3 pseudoislets were washed in phosphate buffered saline (PBS) and cultured overnight at 37° C. in 5 % $CO_2$ in DMEM as described above.

Melt Electrospin Writing (MEW):

Biological grade polycaprolactone (PCL) scaffolds were created by MEW as described previously using a translating x-y stage. Briefly, PCL (Perstorp, $M_n$ ~41 kDa, PDI=1.78) pellets were placed in a Luer lock syringe and heated to 60° C. in an oven overnight to remove air bubbles. A blunt 23 G needle acting as the spinneret was attached to the syringe and placed into an electrical heating system heated to 65° C. The PCL melt was then electrospun using a collector distance of 15 mm, and flow rate of 20 mL/h with a voltage of 10 kV applied to the spinneret. Writing with the PCL fibres (20 µm) was achieved by collecting on a grounded plate connected to a programmable x-y stage, controlled using Mach 3 software.

Preparation of Implants:

For each device, 24 alginate capsules were individually picked and each placed inside a cubic pore (900×900×900 µm) of the PCL scaffold of size 1 cm². The capsules were secured by placing a PCL lid and base (1 cm²) which were heat sealed to the scaffold from four sides. The complete device was placed in DMEM media.

Animal Model:

All animal experiments were approved by University of Sydney Animal Ethics Committee (Protocols 2015/879 and 2017/1237). Immune-deficient NOD/SCID or immune-competent BALB/c mice were housed under normal acclimatising conditions (12 hours dark/light cycle, chow rodent diet and drinking water ad libitum). Some animals (weighing >20 g) were made diabetic by multiple low dose intraperitoneal injections of streptozotocin [STZ; NOD/SCID: 5×40 mg/kg; BALB/c 4×75 mg/kg body weight)]. A subset of the diabetic mice was anesthetised (2-5% isoflurane) and PCL scaffold implanted by subcutaneous surgery on the back near the scapula. Analgesia (0.1 mg/kg buprenorphine and 0.5 mg/kg meloxicam) was administered for 3 days after surgery. Body weight and random blood glucose (tail vein prick) were measured 3 times a week for 4 weeks after which animals were anesthetised, blood collected by cardiac puncture, implanted device and pancreas removed. The implanted device was placed in DMEM (25 mM glucose) and cultured overnight at 37° C. in 5% $CO_2$ for measurement of insulin in the media.

Static Glucose Stimulation:

Incubation in glucose for insulin secretion was conducted on encapsulated pseudoislets and on implanted devices after removal from the host. DMEM (25 mM glucose) was removed from encapsulated pseudoislets/implants, and samples washed with Kreb's Ringer Bicarbonate (KRB) buffer (115 mM NaCl; 4.7 mM KCl; 1.28 mM $CaCl_2$ and 1.2 mM $MgSO_4$) supplemented with 0.1% BSA. This step was followed by 1-hour incubation with KRB with 2.8 mM glucose. Samples were washed in KRB before 1-hour incubation with KRB with 20 mM glucose. All incubations were at 37° C. in 5% $CO_2$. Supernatants were carefully removed after each incubation period and stored at −20° C. Insulin release was measured by mouse insulin ELISA kit (Mercodia, USA) as per manufacturer's instructions.

Histological Assessment:

After implants were removed from mice, they were embedded in OCT medium and stored at −80° C. Sections (10 µm) were placed on slides and fixed with methanol for 5 min. Samples were placedin 100% and 70% and followed by immersion in water. Haematoxylin and eosin (H&E) staining performed as per routine established protocol. To demonstrate collagen deposition, Sirius red staining was performed. Sections were stained 1-hour with picric acid containing 0.1% fast green and 0.1% direct red.

Immunofluorescent Staining:

For localisation of specific proteins OCT embedded samples were sectioned (10 µm) and fixed with methanol for 5 min following 3 washes in Tris-Buffered Saline and Tween 20 (TBST), non-specific sites were blocked by incubation with 1% BSA in TBS (blocking buffer) for 1-hour. The slides were then washed off with TBST prior to overnight incubation in primary antibodies (insulin 1:400, CD31 1:100, NF-κB p65 1:200, MPO 1:100, CD68 1:50, CD19 1:100, α-SMA 1:200) diluted in blocking buffer. The sections were then washed in TBST and finally fluorescent-labelled secondary antibodies (1:1000) diluted in the blocking buffer were added and the slides incubated for 1 hour in the dark. The sections were washed in TBST, briefly dried and mounted in Prolong-Gold mounting media containing DAPI (Molecular Probes, OR, USA).

Results

Figure 1:
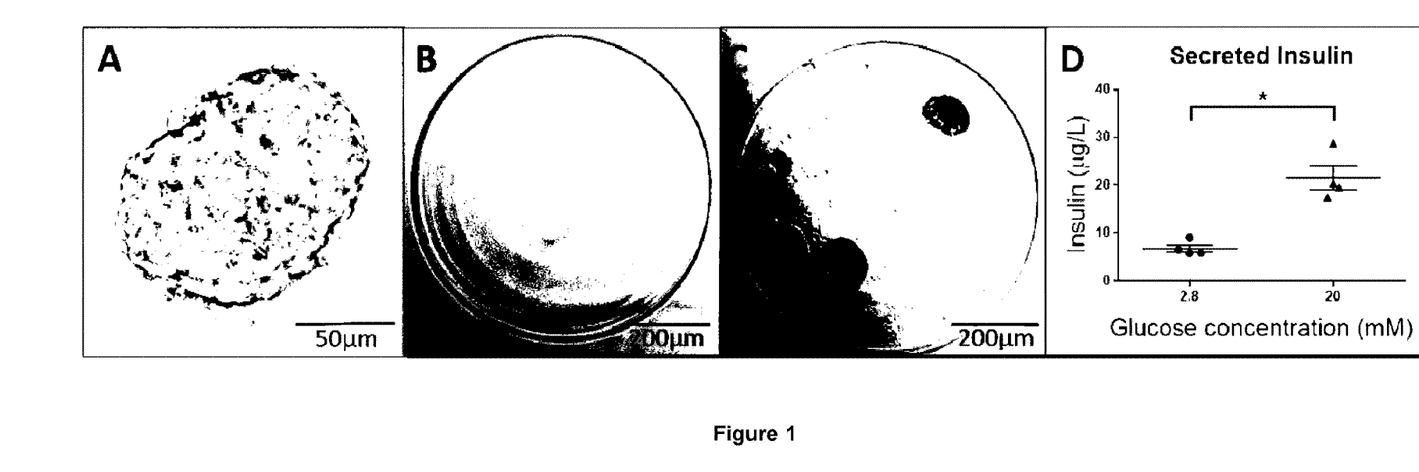
FIG. 1: MIN6 pseudoislet formation, encapsulation and simulation by glucose. (A) MIN6 pseudoislets were formed by growing cells in suspension culture. (B) Capsules formed by passing air through 2.2% alginate solution, followed by gelling in a $BaCl_2$ bath. (C) MIN6 pseudoislets encapsulated in alginate, and (D) their responsiveness to change in glucose concentration to secrete insulin into the media measured. Data: mean±s.d., p<0.05, Mann-Whitney U-test.

Pseudoislet Formation and Encapsulation:

MIN6 cells were grown as a suspension culture for 5 days to generate self-forming aggregates or pseudoislets (FIG. 1A). These structures are similar in size (135±44 µm diameter, n=8) to normal mouse islets. Alginate capsules of 755±49 µm diameter (FIG. 1B) were generated. Between 1 and 3 pseudoislets were contained within these capsules (FIG. 10). A sample of 10 randomly selected capsules (containing 1-3 islets) were tested for insulin secretion in response to change in glucose concentration. As shown in FIG. 1D increasing glucose concentration from 2.8 to 20 mM caused ~3-fold increase (p=0.02, n=4/treatment) in insulin secretion by the encapsulated MIN6 pseudoislets.

Figure 2:
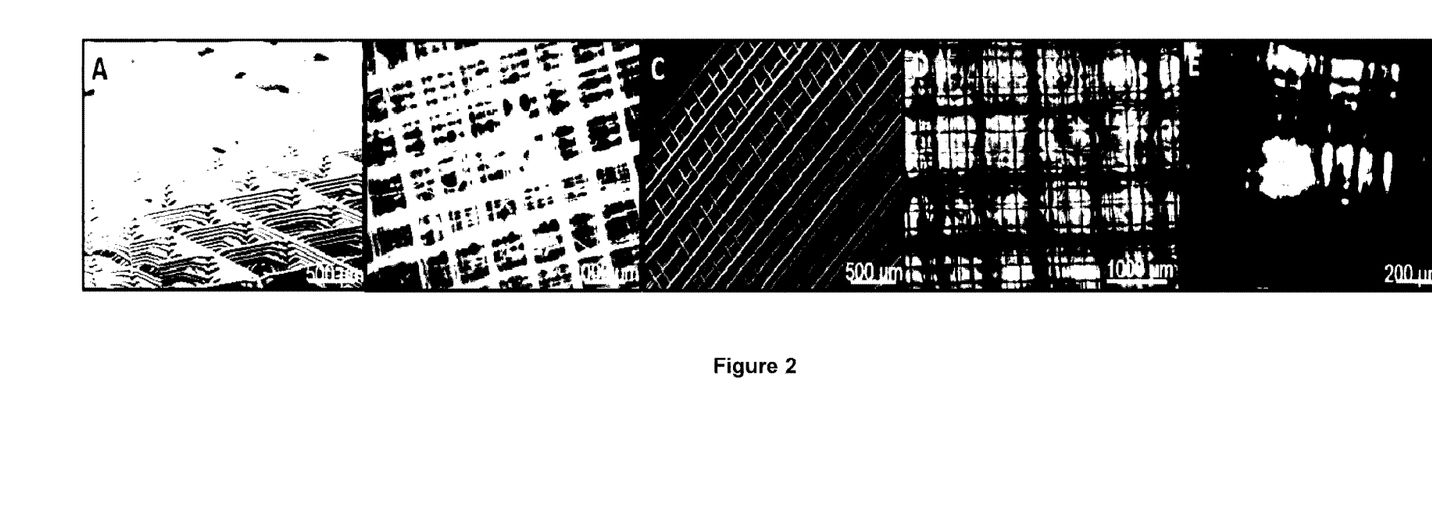
FIG. 2: PCL scaffold created by melt electrospin writing. (A) Scaffold of height 1.5 mm containing multiple cubic pores of dimension 0.9×0.9×0.9 mm. (B) Each alginate microcapsule slotting into a cubic pore. (C) The body of scaffold together with less porous base region prior to fusing it with the body and (D) a high power view of the complete device with microcapsules visible inside it. (E) Mouse islets retain their viability in microcapsules when placed in PCL scaffolds kept in tissue culture. Green fluorescent staining of CFDA shows the cells are alive; there was no staining of the red dye PI, which would have indicated cell death.

Scaffold Printing:

Scaffolds were created by the process of MEW using PCL. The structure consists of a lattice of cubic pores. Each cubic pores has dimensions 0.9×0.9×0.9 mm, as shown by scanning electron micrograph (FIG. 2A), and is sufficient to contain a spherical alginate capsule which can be slotted into the cubes. The scaffold and the associated alginate capsules were secured by a base and lid structure (FIG. 2C) on the top and bottom. The base and lid were also printed using MEW but contained smaller cubic pores. The base region and the centre region were printed together, whereas the lid was separately printed and heat sealed to the rest of the scaffold. The completed scaffold is shown in FIG. 2D. The PCL scaffold enhanced cell viability, evident from mouse islet cells staining green (viable) with CFDA and not red (dead) with PI after placing in the scaffold and incubation in vitro (FIG. 2E).

Figure 3:
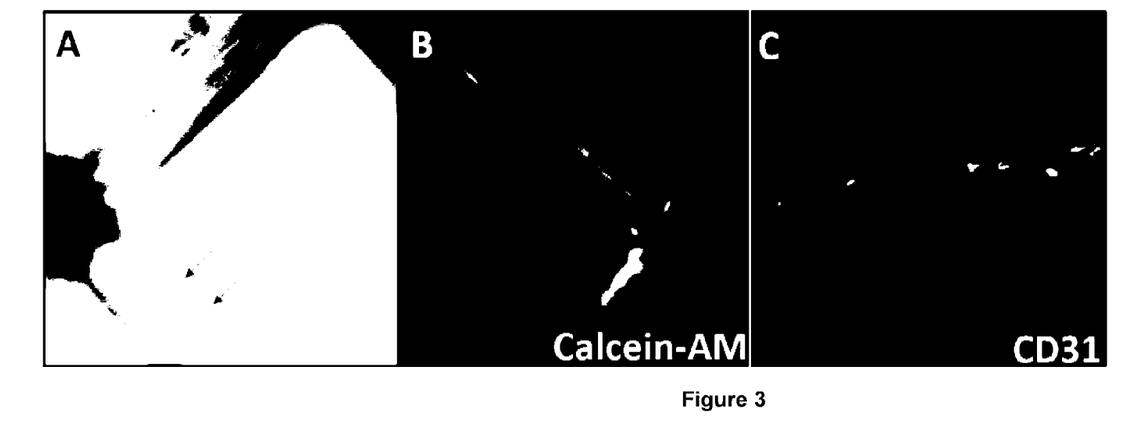
FIG. 3: Potential of PCL scaffolds for vascularisation. (A) HUVEC attach (arrows) to fibres of PCL scaffolds within 24 hours of seeding. (B, C) In cultures of >7 days the associated cells remain viable as observed by fluorescence of Calcein-AM, and retain expression of vascular endothelial cell marker CD31.

PCL Scaffold Encourage Endothelial Cell Attachment:

The main purpose of the scaffold was to promote angiogenesis when implanted in vivo. To enhance angiogenesis, it is necessary for endothelial cells to adhere to the strands of the scaffold. Adhesiveness to PCL scaffolds was tested in vitro with human umbilical vein endothelial cells (HUVEC). These cells readily attached to PCL, maintain viability and expressed endothelial cell marker CD31 (FIG. 3A-C).

Figure 4:
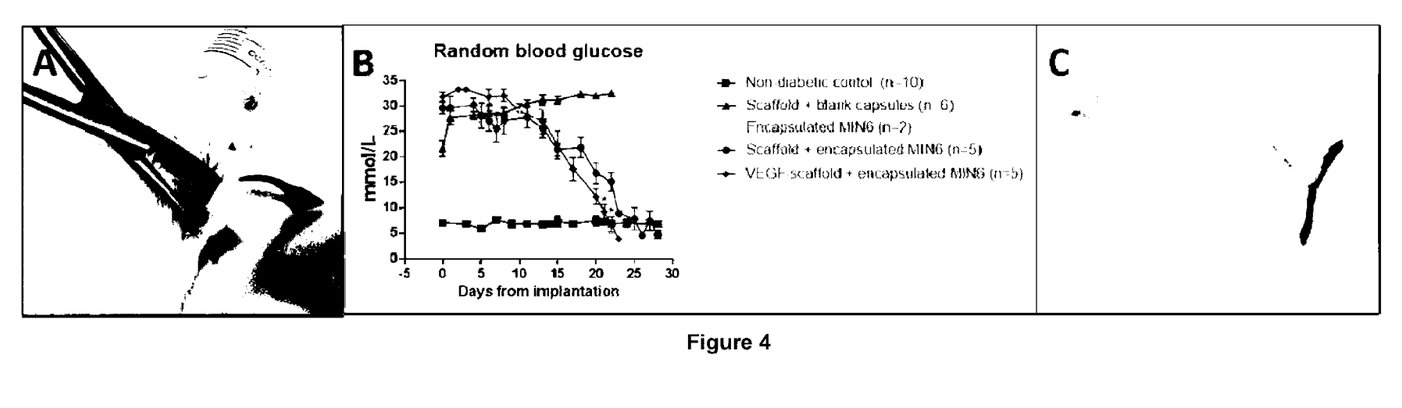
FIG. 4: Effect of implantation of PCL scaffold in diabetic mice. (A) PCL scaffold containing encapsulated MIN6 pseudo-islets were subcutaneously implanted in diabetic NOD/SCID mice and retained for 4 weeks. (B) Hyperglycaemia in diabetic mice implanted with scaffolds containing encapsulated insulin-producing cells (red) was normalized to blood glucose levels of non-diabetic mice (blue). When the scaffolds were coated with a factor that promotes blood vessel formation (VEGF, purple) normalization of blood glucose was faster (red vs purple). In contrast, encapsulated insulin-producing cells implanted without a scaffold in diabetic did not normalize glucose levels (green). (C) Scaffold removed from mice post implantation showed formation of blood vessel (arrow).

Normalisation of Blood Glucose by Subcutaneous Implantation:

PCL scaffolds containing either encapsulated MIN6 pseudoislet or empty alginate capsules were implanted subcutaneously in STZ-treated diabetic NOD/SCID mice (FIG. 4A). The wound site was closed and mice followed for approximately 4 weeks. Body weight and random BGL were measured 3 times a week. Non-STZ treated mice served as non-diabetic controls (NDC). BGL ranged between 6-9 mmol/L in NDC mice over the study period, whereas in diabetic mice implanted (DI) with encapsulated MIN6, mean BGL reached ~30 mmol/L at the time of implantation and gradually started to decline 5-7 days post implantation. The decreasing trend continued, resulting in a lowering of BGL to 4 mmol/L (FIG. 4B). Implants from these mice were removed as shown in FIG. 4C. There was growth of fibrofatty tissue in and around the scaffold, and formation of blood vessels were also observed.

Figure 5:
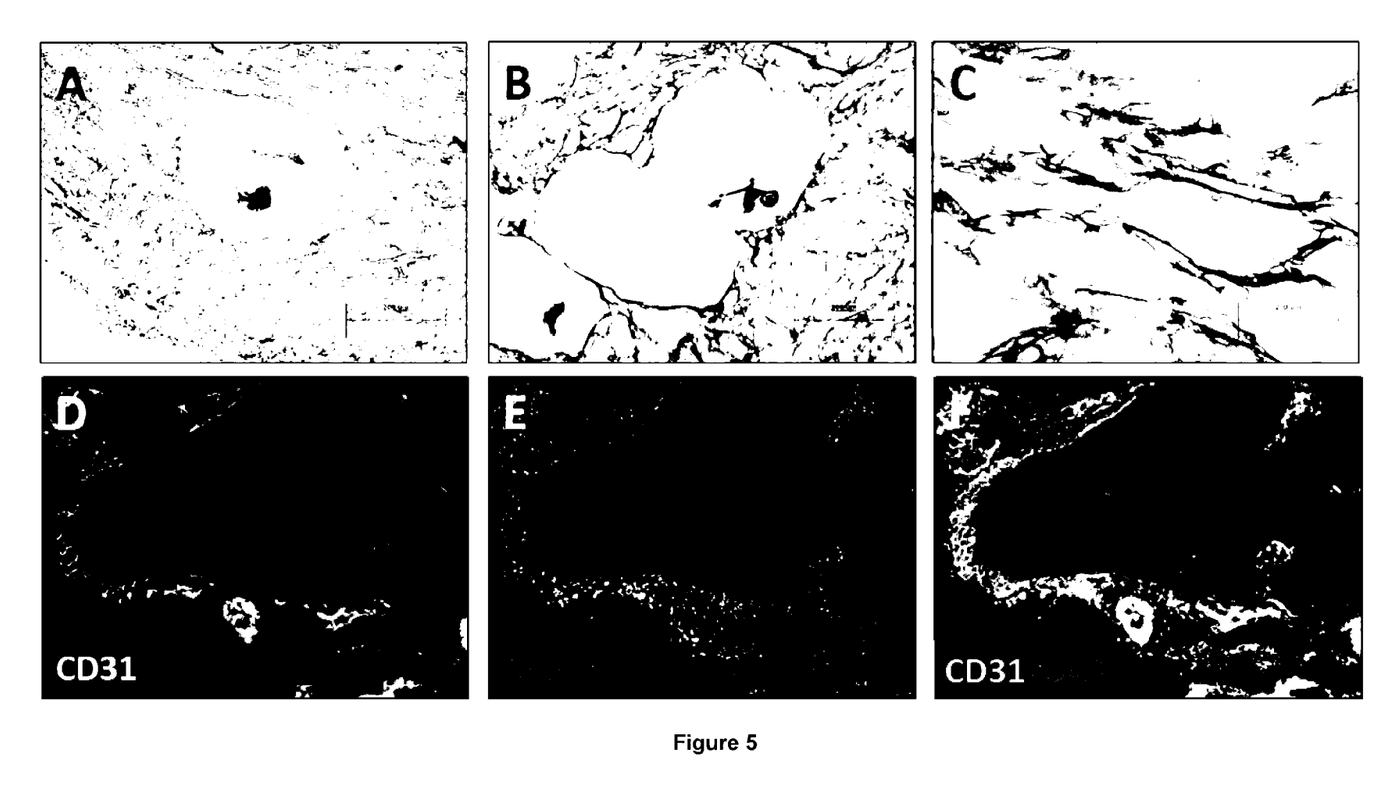
FIG. 5: Histology assessment of explanted scaffolds. (A) H&E staining of explanted scaffold containing encapsulated MIN-6 pseudoislets. (B) Sirius red stain showing areas of collagen deposition (pink) forming an ECM around the alginate capsules and throughout the scaffold. (C) Higher magnification of Sirius red stain showing attachment of cells to PCL fibres and collagen deposition crosslinking them. (D) CD31 staining showing blood vessel formation, (E) DAPI stain of the same region and (F) merged image of CD31 and DAPI.

PCL Scaffold Promotes Cellular Infiltration and ECM Formation:

Histological assessment of explanted scaffolds by H&E staining (FIG. 5A) showed large populations of infiltrated cell throughout the implanted device. These were not inflammatory infiltrates as confirmed by negative staining of myeloperoxidase expressing polymorphonuclear cells and F4/80 expressing monocyte/macrophages (not shown). Rather, they were mostly fibroblast as evident from the large amount of collagen deposition around the PCL as shown by pink areas of Sirius red staining (FIG. 5 B and C). Cells not only infiltrated the scaffolds, but attached to the PCL strands as observed under high magnification (FIG. 5C).

The formation of blood vessels was confirmed within the scaffolds, with staining for the vascular endothelial cells marker CD31. FIG. 5D illustrates classical chicken-wire like expression of CD31, as seen on blood vessels (arrow). CD31 expression was also seen on the cross-section through a blood vessel (circle).

Figure 6:
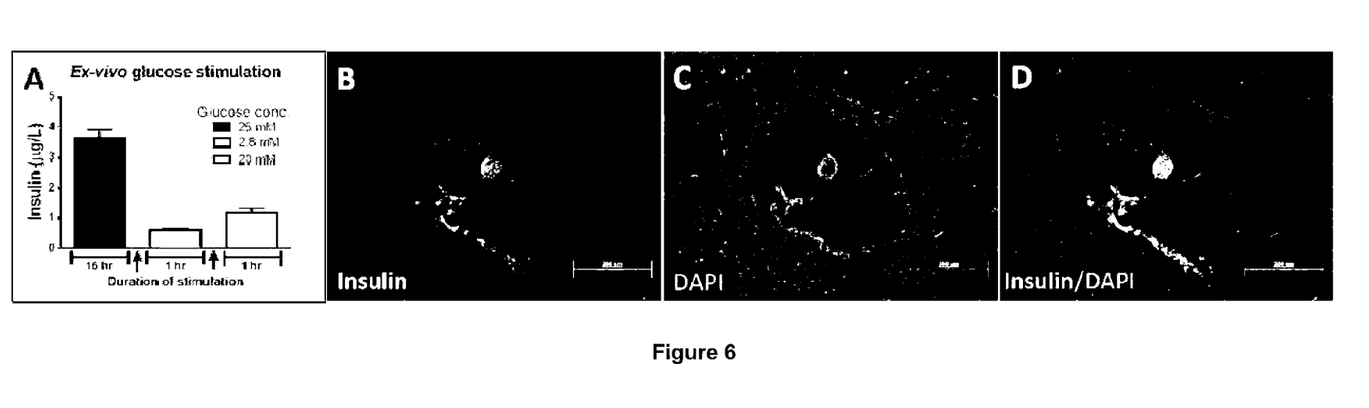
FIG. 6: Insulin production from implants. (A) Encapsulated cells within the scaffolds continue to respond to glucose stimulation ex vivo when scaffolds were incubated in 25 mM glucose (16 hr) followed by 2.8 and 20 mM glucose (1-hour each). Culture media collected after each incubation to measure insulin by ELISA, and scaffolds washed (arrow) in between change of media. Data: mean±range (B) Insulin staining within pseudoislets placed in the PCL scaffold. (C) Cell population stained with DAPI and (D) Merged image showing insulin production from encapsulated cells.

Encapsulated MIN6 Pseudoislets Maintain Expression and Secretion of Insulin:

The grafts were explanted at 4 weeks, and incubated overnight in 25 mM glucose, followed by 1-hour static stimulation using 2.8 or 20 mM glucose. Insulin in the media was measured. FIG. 6A shows mouse insulin was released from the explants, in a glucose concentration (and time) dependent manner. Using immunostaining it was confirmed that the encapsulated MIN6 cells were producing insulin. As shown in FIG. 6B-D, the encapsulated pseudoislets stained positively for insulin.

EXAMPLE 2

PCL Scaffold Associated Insulin Cells Produce and Release Insulin

Figure 7:
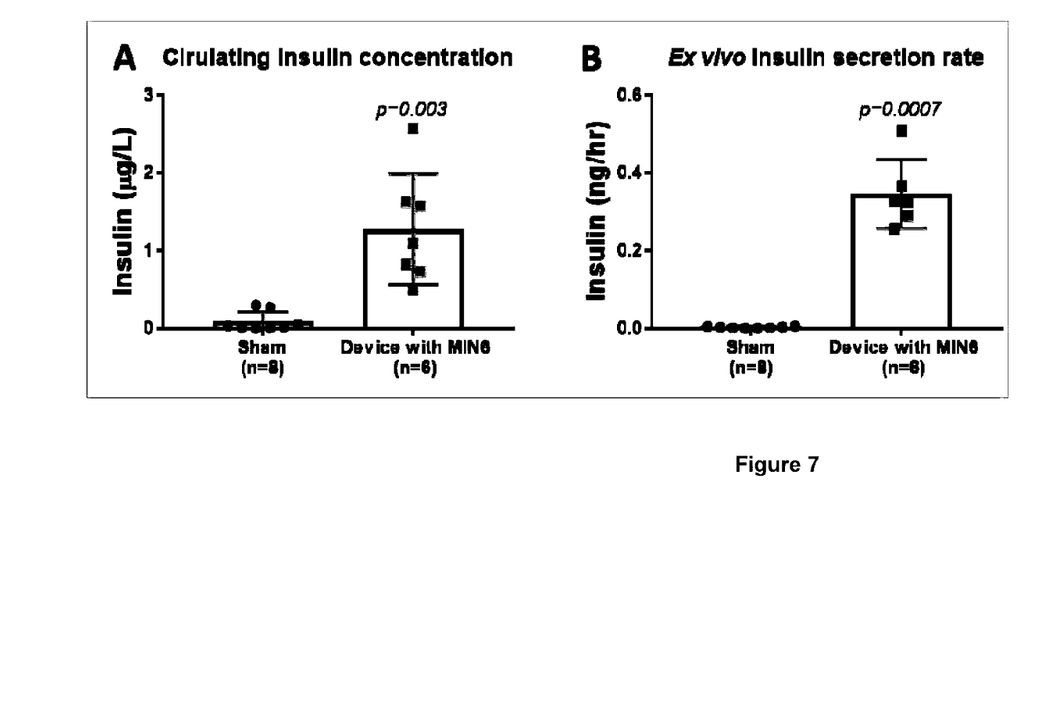
FIG. 7: Detection of mouse insulin in diabetic NOD/SCID mice implanted with either sham scaffolds or scaffolds associated with MIN6 cell clusters. (A) Circulating concentration of mouse insulin at termination. (B) Rate of insulin release from grafts in culture. P<0.01 using Mann-Whitney Utest.

Diabetic NOD/SCID mice were implanted subcutaneously with either a sham implant or PCL scaffold containing MIN6 clusters (as previously described in Example 1). At termination of experiment, blood was collected from mice and plasma extracted to measure circulating concentration of mouse insulin using an ELISA (Mercodia, Uppsala, Sweden). FIG. 7A shows trace amounts of endogenous mouse insulin in sham mice, but significantly higher concentrations of insulin in animals implanted with PCL scaffold containing MIN6 cells.

The implants were taken out from animals and cultured for 16 hours in serum free DMEM at 37° C., 5% $CO_2$ To determine if the implants secreted insulin, the media was assayed for mouse insulin. As shown in FIG. 7B sham implants secreted no insulin, whereas PCL scaffold implants containing MIN6 cells in the device secreted insulin at a mean rate of 0.35 ng/hr.

Implants Produce Insulin in Immune Competent BALB/c Mice

Figure 8:
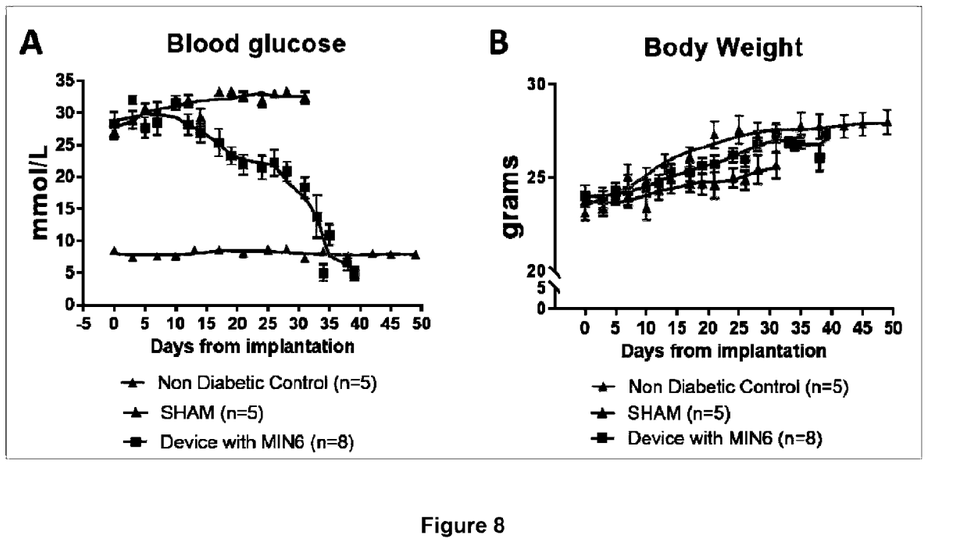
FIG. 8. Effect of implanted scaffold-associated cells on (A) blood glucose and (B) body weight of immune competent BALB/c mice.

We tested if the scaffold-associated insulin-producing MIN-6 cells implant could function in BALB/c mice that have a normal immune system (immune competent) and with a major histocompatibility difference from the cells (H-2Kd and H-2Kd respectively). BALB/c mice were made diabetic using streptozotocin (4×75 mg/kg) and either a sham implant or the scaffold-associated MIN6 cell implant (approximately 50 MIN6 clusters in 24 microcapsules) was implanted subcutaneously. Blood glucose level (BGL) and body weights were monitored and compared to healthy non-diabetic control mice (FIG. 8, green line). FIG. 8A shows, in healthy mice mean blood glucose remained ~8 mmol/L throughout experimental duration. In diabetic mice BGLs were >25 mmol/L on the day of implantation. In mice with sham implants BGL remained high (black line), but those implanted with scaffolds containing MIN6 cells (blue line) BGL was gradually lowered to normal levels between 33 and 39 days post-implantation.

All mice had similar body weights at start of experiment and showed increase in body weight during experimental duration (FIG. 8B). Weight gain was highest in non-diabetic control mice (green), and least in diabetic mice with sham implant (black). In diabetic mice implanted with MIN6 cells (blue) weight gain was greater compared to sham.

Figure 9:
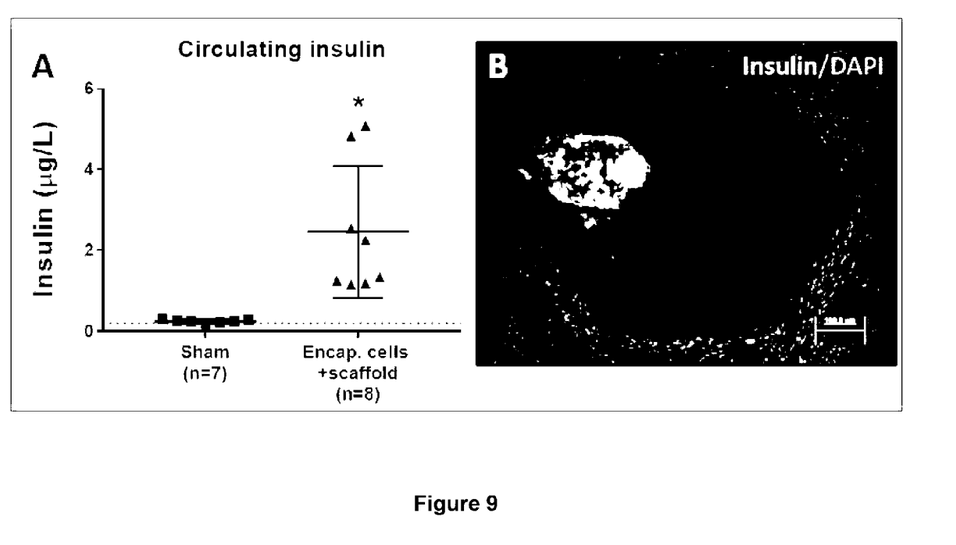
FIG. 9: Insulin production from implanted scaffold-associated cells (A) Circulating concentration of mouse insulin in diabetic mice f*P<0.01 vs sham, by ANOVA. Dotted line: assay detection limit; Shaded area: circulating range of insulin in healthy mice. (B) Ex vivo immune staining of insulin (green) located within MIN6 pseudo-islets inside a microcapsule.

Similar to the NOD/SCID mice, elevated levels of insulin in plasma of mice receiving treatment was measured (FIG. 9A) and confirmed ex vivo presence of insulin within encapsulated cells of the implant (FIG. 9B).

PCL Scaffold Facilitates Vascularisation in BALB/c Mice

Figure 10:
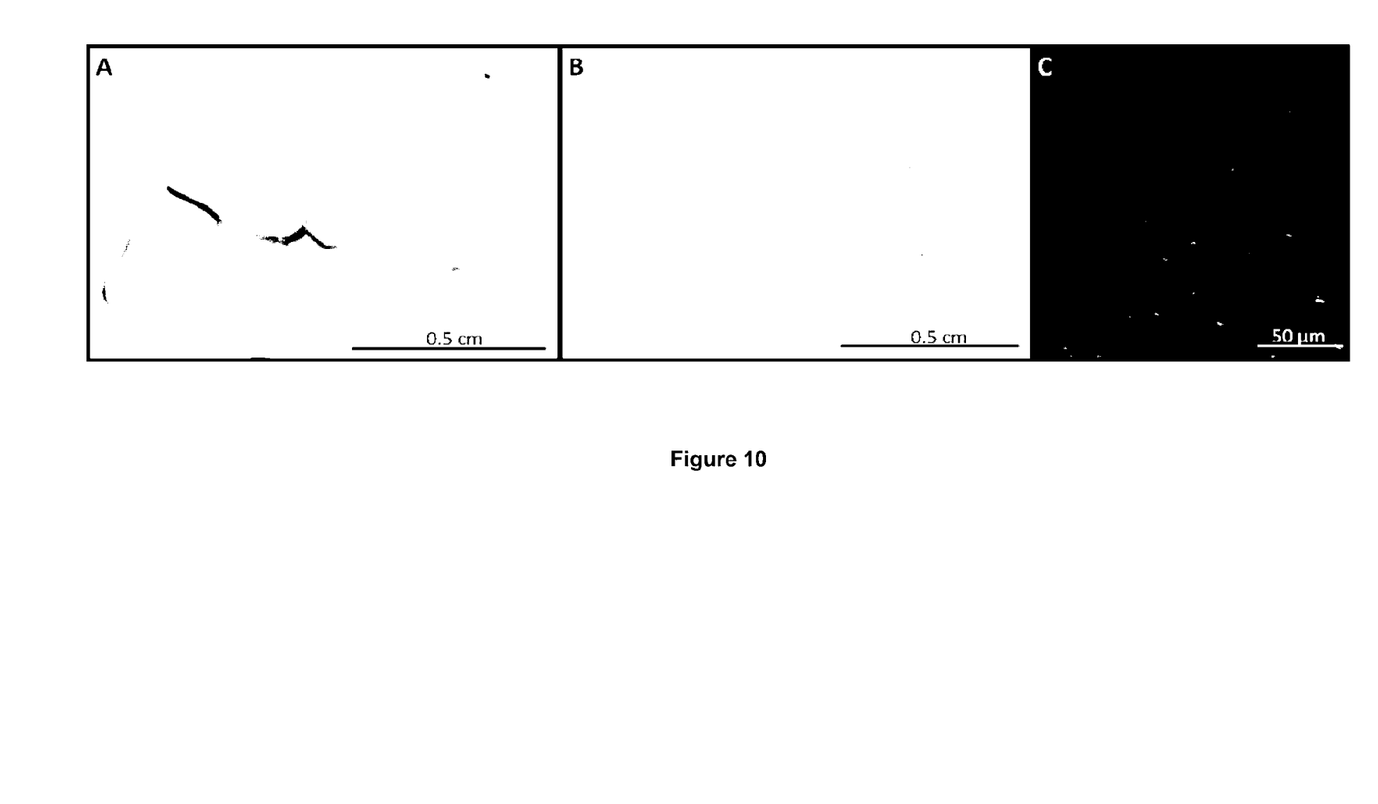
FIG. 10: Vascularisation of implanted scaffold. Blood vessels were clearly visible (A) macroscopically on the side of the implant proximal to the skin and (B) on the side distal to the skin. (C) Blood vessels in red and nuclei in blue inside the implant as visualised by multiphoton intravital microscopy.

Blood vessels were clearly visible macroscopically on implants on the side proximal (FIG. 10A) and on the side distal to the skin (FIG. 10B). Blood vessels (red) within the scaffold was visualised by multiphoton intravital microscopy (FIG. 10C). Dextran (70 kDa)-Texas Red conjugated and DAPI were injected into mice via the tail vein and device visualised after 1 hour.

PCL Scaffold Associated Cells have Reduced Host Cell Response

Figure 11:
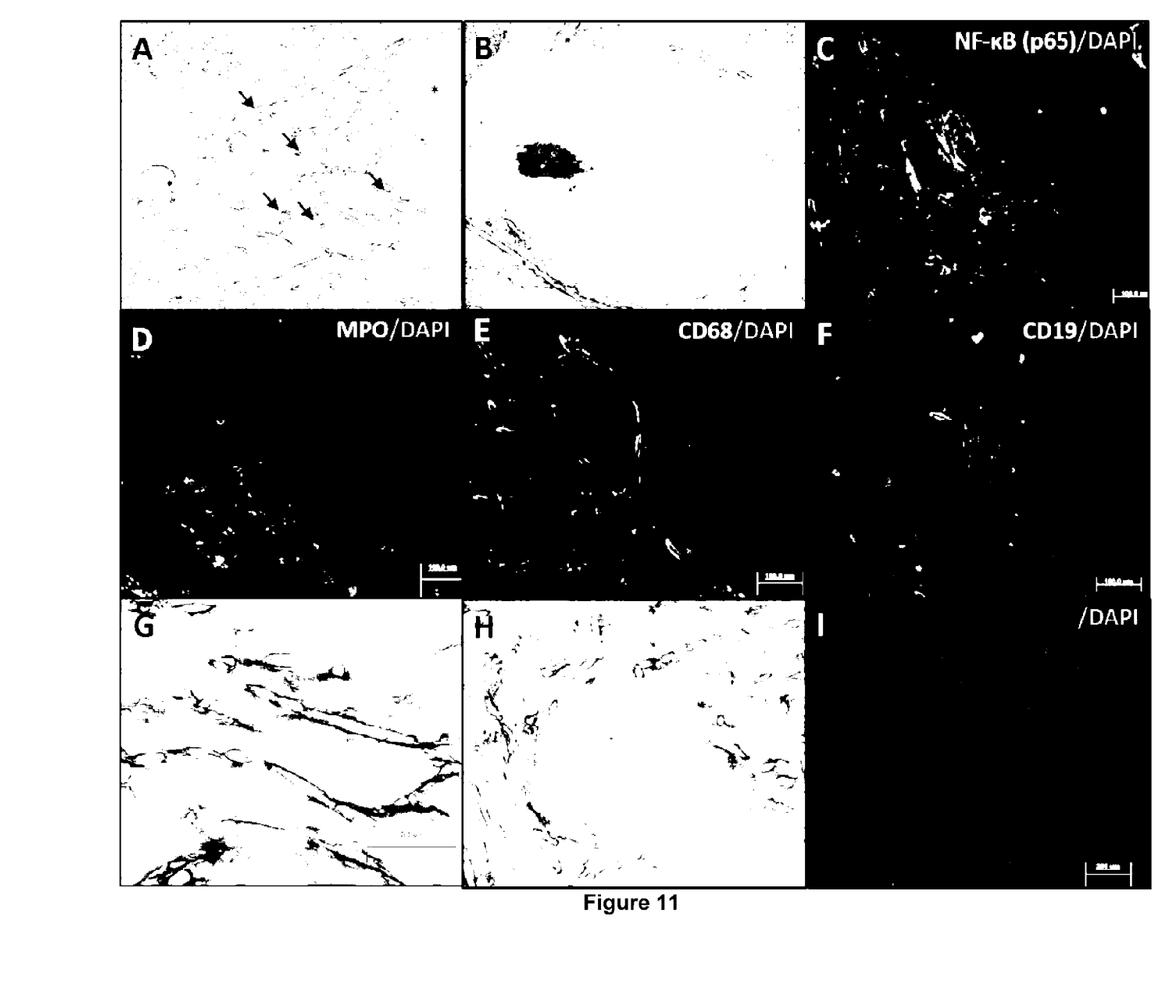

To examine FBR (foreign body reaction) ex vivo implants were used. Data is shown from immune-competent BALB/c mice. Histology of the implants was studied by haematoxylin and eosin (H&E) stain, which showed abundant cellular infiltration into the device (FIG. 11A). Often clusters of cells typical of inflammatory foci were seen along or adjacent to PCL scaffolds (FIG. 11A arrows), though these foci were not seen around the micro-capsules (FIG. 11A*,B). NF-kB p65 immuno-stain was used to confirm pro-inflammatory cells were predominantly localised to the scaffolds (FIG. 11C). These inflammatory infiltrates were comprised mainly of neutrophils and monocytes/macrophages (FIG. 11D,E respectively). Occasionally, small numbers of B-lymphocytes (FIG. 11F) were observed, but CD4+ T-lymphocytes were undetectable (not shown). Consistent with the histology and NF-kB p65 expression, the cell specific markers were localised to the scaffolds. Sirius red stain on device shows ECM deposition of collagen (pink) (G) interconnecting the strands of the scaffold, and (H) around microcapsules. (I) α-SMA+ myofibroblasts showing area of active fibrogenesis around microcapsules and in the scaffold.

EXAMPLE 3

Figure 12:
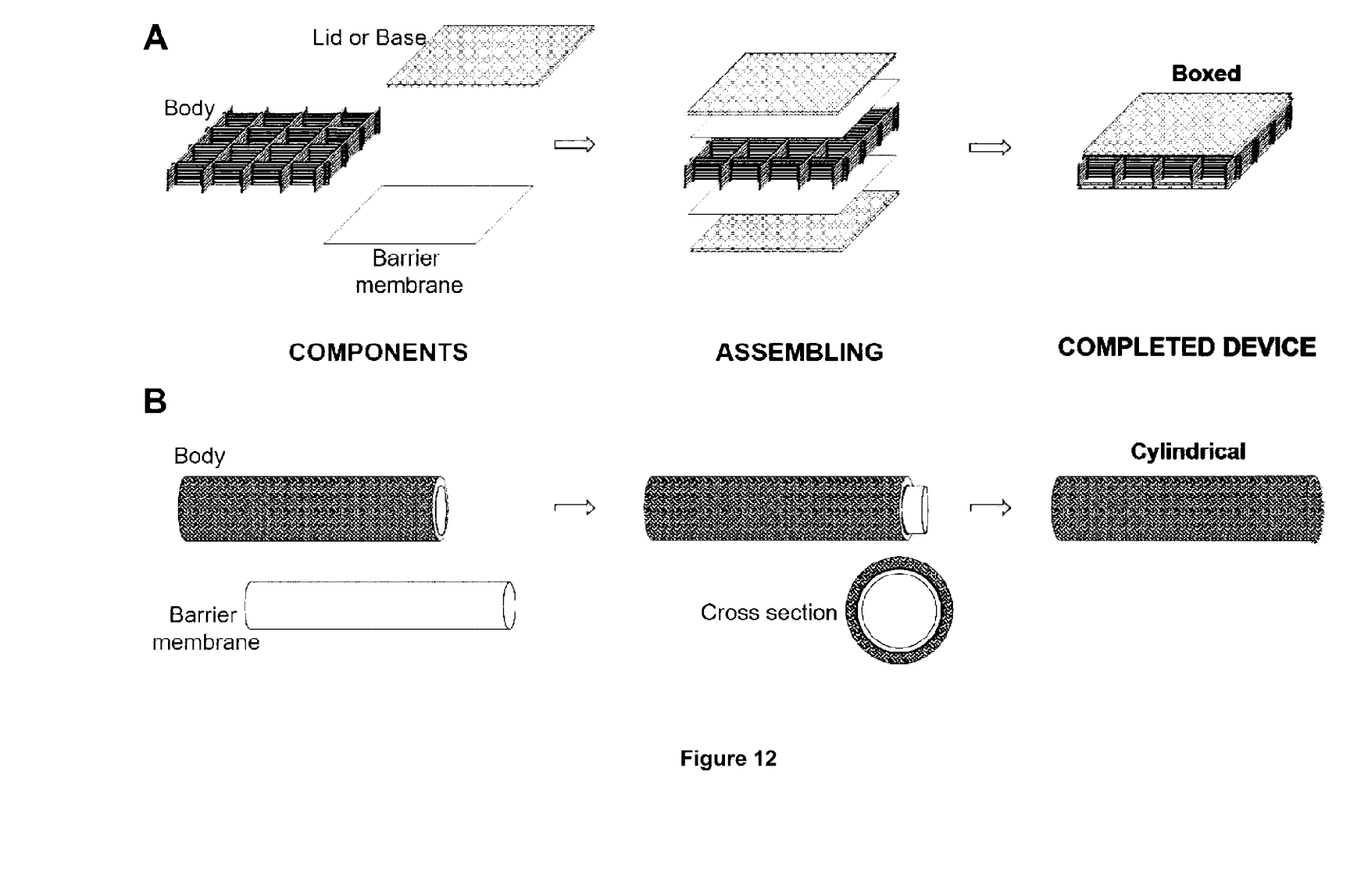
FIG. 12: Schematic showing MEW printed scaffolds that may include barrier membranes to prevent poential escape of cells from within devices. (A) Boxed configuration of device with a body, lid and base. Barrier membrane may be placed between the body and lid/base (B) Cylindrical configuration of device with a hollow core where a barrier membrane can be inserted.

An implant was designed to include a barrier region with pore size 0.5-20 µm to further stop encapsulated cells from leaving the centre region after implantation. The barrier region may be manufactured from the same or different materials as the rest of the scaffold using MEW by depositing the fibres with narrow spacing (<100 µm) in a geometric pattern to allow for the 0.5-20 µm porosity. Alternatively, a barrier region in the form of a membrane may be commercially available or one may be made using established techniques (e.g. fibre weaving, ion beam or particle ablation, templating, phase separation). Examples of scaffolds comprising barrier regions are shown in FIG. 12.

What is claimed is:

1. A method for delivering an agent to a subject consisting of associating cells that produce said agent with a scaffold, and implanting said scaffold-associated cells subcutaneously in said subject, wherein the scaffold increases vascularisation at the site of subcutaneous implantation when compared to subcutaneous implantation of the same cell type without said scaffold and enhances the viability of the scaffold-associated cell after implantation by promoting vascularization at the site of implantation, and wherein the cells are encapsulated,
   wherein the scaffold comprises a lid region or a base region comprising cubic pores with maximum dimensions ranging from 5 µm to 25 µm, and a centre region comprising cubic pores with maximum dimension of 2000 µm and a minimum dimension of at least 500 µm, wherein the pores of the centre region are large enough to allow a single encapsulated cell to be housed.

2. The method of claim 1, wherein the scaffold comprises biocompatible fibres, which are 10-50 µm thick.

3. The method of claim 2, wherein the fibres are produced by 3D-printing by melt electrospin writing.

4. The method of claim 1, wherein the scaffold comprises pores that become traversed by blood vessels within at least 10 weeks after being implanted subcutaneously.

5. The method of claim 3, wherein the scaffold reduces or delays the host cell response of the subject to the scaffold-associated cells when compared to the host cell response of the subject to the same cell type implanted subcutaneously without said scaffold or said encapsulation.

6. The method of claim 5, wherein the cells are encapsulated in alginate.

7. The method of claim 5, wherein a deficiency of said agent is a causative factor of a disease or disorder selected from the group consisting of diabetes, liver failure, and Parkinson's disease.

8. The method of claim 7, wherein the disease or disorder is diabetes.

9. The method of claim 8, wherein the agent is selected from the group consisting of insulin, an insulin analog, or a precursor of insulin, such as preproinsulin or proinsulin.

10. The method of claim 9, wherein the scaffold-associated cells are pancreatic cells.

11. The method of claim 1, wherein the scaffold comprises a lid region and a base region arranged at opposite sides of the scaffold.

12. The method of claim 1, wherein the scaffold comprises a boxed configuration.

13. A method of treating diabetes, consisting of implanting an encapsulated cell associated with a scaffold subcutaneously, where said cell releases insulin, an insulin analog, or a precursor of insulin, wherein the scaffold increases vascularisation at the site of subcutaneous implantation when compared to subcutaneous implantation of the same cell type without said scaffold and enhances the viability of the scaffold-associated cell after implantation by promoting vascularization at the site of implantation, and wherein the cells are encapsulated,
   wherein the scaffold comprises a lid region or a base region comprising cubic pores with maximum dimensions ranging from 5 µm to 25 µm, and a centre region comprising cubic pores with maximum dimension of 2000 µm and a minimum dimension of at least 500 µm, wherein the pores of the centre region are large enough to allow a single encapsulated cell to be housed.

14. The method of claim 13, wherein the cell is encapsulated in alginate before being associated with said scaffold.

* * * * *